United States Patent [19]

Kusy

[11] 4,295,374

[45] Oct. 20, 1981

[54] SPECIMEN GRIPS FOR DYNAMIC MECHANICAL ANALYZER

[75] Inventor: Robert P. Kusy, Chapel Hill, N.C.

[73] Assignee: E. I. Du Pont de Nemours and Company, Wilmington, Del.

[21] Appl. No.: 74,092

[22] Filed: Sep. 10, 1979

[51] Int. Cl.³ .............................................. G01N 3/32
[52] U.S. Cl. .................................................... 73/579
[58] Field of Search ................ 73/579, 580, 581, 808, 73/812-815, 856, 859, 860, 574-578

[56] References Cited

U.S. PATENT DOCUMENTS

| | | | |
|---|---|---|---|
| 1,908,258 | 5/1933 | Klopsteg | 73/579 X |
| 2,849,877 | 9/1958 | Burgett et al. | 73/808 |
| 2,960,862 | 11/1960 | Spurr et al. | 73/579 |
| 3,224,259 | 12/1965 | De Nicola | 73/860 X |
| 4,034,602 | 7/1977 | Woo et al. | 73/579 |
| 4,170,141 | 10/1979 | Woo | 73/812 X |

Primary Examiner—James J. Gill

[57] ABSTRACT

Specimen clamps or grips for locating and releasably retaining a specimen for testing on a dynamic mechanical analyzer which analyzer is of conventional construction with the improvement being in the specimen clamps.

4 Claims, 7 Drawing Figures

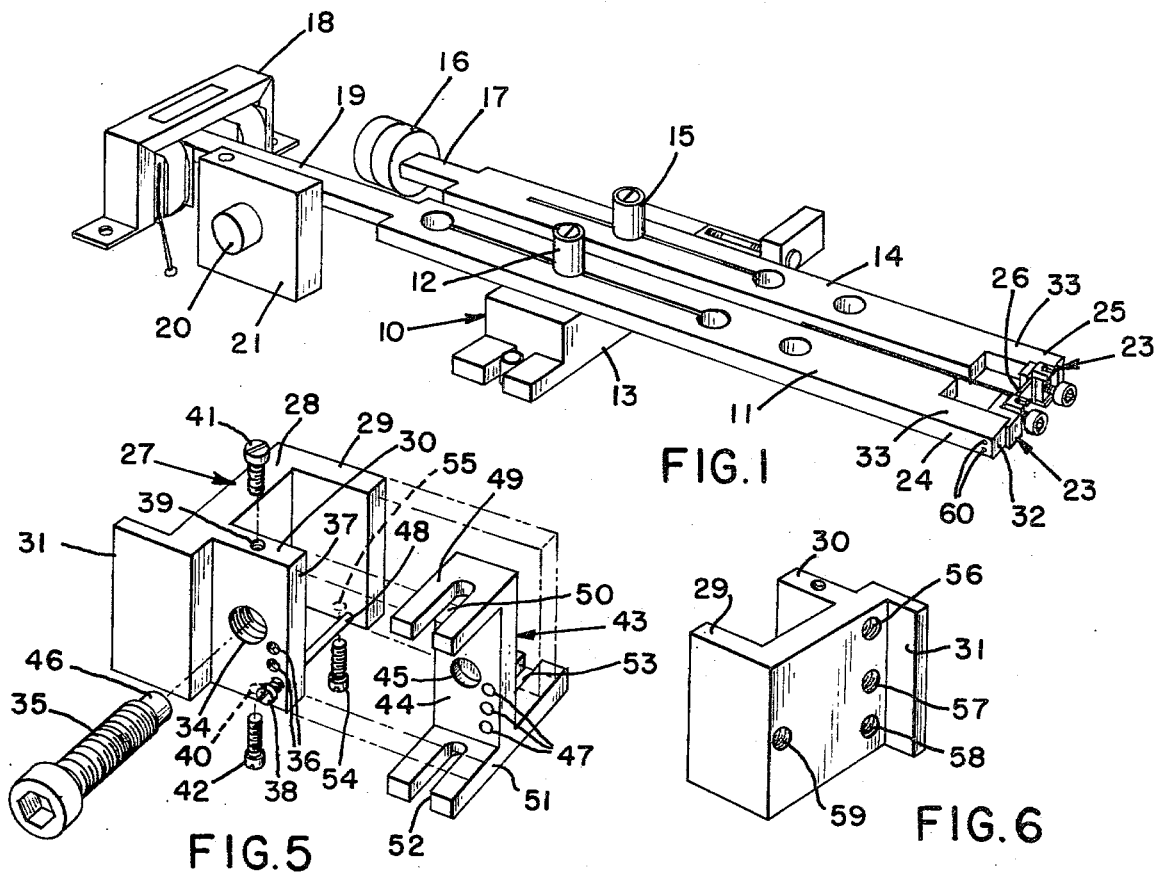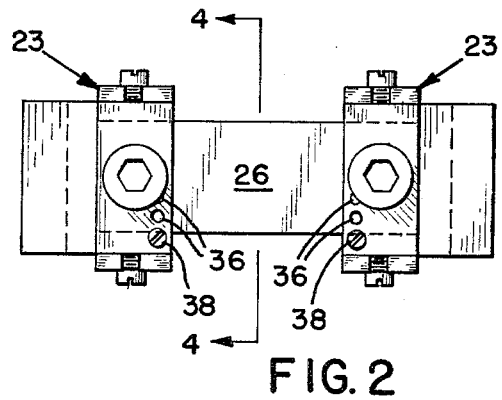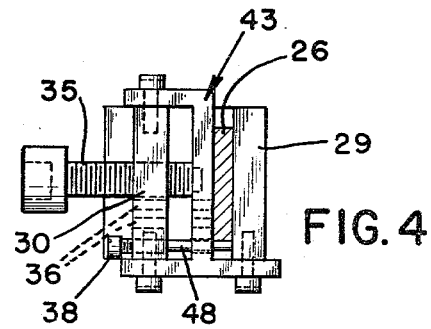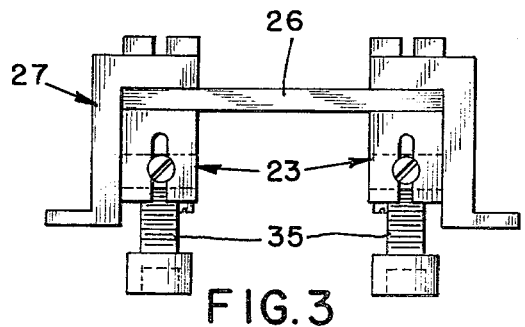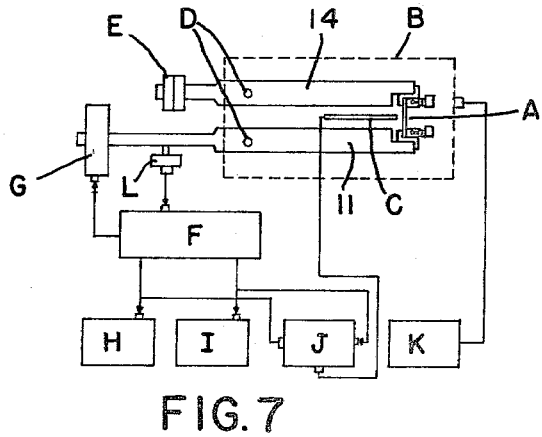

SPECIMEN GRIPS FOR DYNAMIC MECHANICAL ANALYZER

BACKGROUND AND ADVANTAGES OF THE PRESENT INVENTION

Presently the dynamic mechanical analyzer of Du-Pont Instruments which is purportedly disclosed in U.S. Pat. No. 3,751,977 is for determining properties of a material including resonant frequency, energy dissipation modulus, crystallinity, plasticizer effectiveness, creep and stress relaxation, elastic shear modulus, mechanical hysteresis, among other material properties and characteristics. Spaced arms hold the sample by means of clamps or grips that are interconnected by the sample, and the clamps are carried by driven and driver supporting arms. An electromechanical transducer sets the driver arm into vibratory motion which is transmitted through the sample to the driven support arm that is counter-balanced. The specimen is placed either in flexure or shear stress and when the displacing force is released, the deflection energy in the specimen produces a resonant oscillation with the frequency and amplitude being sensed by a linear variable differential transformer that is positioned at the opposite end of the drive arm. The information derived is fed to the dynamic mechanical analyzer driver circuitry which feeds back enough energy to the electromechanical transducer to keep the sample in oscillation at a constant amplitude.

The structure of prior clamps or grips is such that uneven pressure is applied to the test specimen utilizing two clamping screws on each grip which may frequently fracture delicate specimens. The present form of modified C-type clamp permits the specimen to slide, rock and drop readily. No provision is made for centering the specimen of any predetermined size and only a minimum range of sample specimens may be accommodated.

The present invention for an improved specimen clamp or grip eliminates many of the disadvantages and drawbacks of clamps currently used by providing clamping members that readily center the specimen to be tested and provides more uniform clamping stress on the specimen.

Another objective of the improved specimen clamps is the elimination of any uneven pressure, rocking motion and specimen dropping.

Further objectives and advantages of the improved specimen clamps are that they may be accommodated readily to the driver and driven sample supporting arms utilizing similar mass moment of inertia of the system with minimum analyzer modifications as for example to the machine constants.

Yet a further objective of the invention is the provision of a plurality of discrete specimen supporting dimensions that will automatically accommodate specimens of specific widths and greater thicknesses.

Other objectives and many of the attendant advantages of the improved clamp or grips for test specimens will become more readily apparent to those skilled in the art of material testing and particularly in utilization of the dynamic mechanical analyzer from the following detailed description taken in conjunction with the accompanying drawing, and mechanical equivalents are contemplated in the attendant claims.

BRIEF DESCRIPTION OF DRAWING

FIG. 1 is a diagramatic perspective view of a dynamic mechanical analyzer with the clamps retaining a test specimen;

FIG. 2 is an enlarged right end elevational view of the clamps of FIG. 1 with a test specimen in position;

FIG. 3 is a top plan view of FIG. 2;

FIG. 4 is a transverse sectional view taken along line 4—4 of FIG. 2;

FIG. 5 is an exploded perspective view of a single clamp member with its components;

FIG. 6 is a perspective view of a body member only of FIG. 5 rotated approximately 180°; and FIG. 7 is a schematic diagram of the dynamic mechanical analyzer with a sample supported by the clamps.

DETAILED DESCRIPTION OF THE PREFERRED EMBODIMENT OF THE INVENTION

Referring to the drawing and particularly to FIG. 1, there is illustrated a dynamic mechanical analyzer 10 of the type sold by DuPont Instruments for use by scientists and engineers for measuring the resonant frequency and energy dissipation with minimal strain on a wide range of material specimens. A driven sample arm 11 is pivotally mounted on the flexure pivot 12 that is supported on the mounting base 13. A cooperating sample arm 14 is also supported on a flexure pivot 15 that is also supported on the base member 13 with the arms 11 and 14 being supported substantially parallel to each other and in the same plane. The arm 14 is a passive arm and is provided with a counterweight 16 at the remote end 17 thereof.

An electromechanical transducer 18 is positioned at the opposite end 19 of the active arm 11 with the frequency and amplitude of oscillation of the active arm being sensed by a linear variable differential transformer 20 supported in the housing 21 for feeding back enough energy to the electromechanical transducer to keep the sample in oscillation at constant amplitude through the dynamic mechanical analyzer driver circuitry.

As illustrated schematically in FIG. 7, the specimen A to be tested may, if desirable, be positioned in a furnace B in which there is a thermocouple C that is connected to a recorder J. The active and passive arms 11 and 14 are supported on the flexure pivots D with the passive arm supporting the counterweight E. The active arm is connected to the electromechanical transducer G. The driver F is connected to the electromechanical transducer G and is controlled by the circuitry from the linear variable differential transformer L. A damping display I is connected to the driver F as is the frequency display H. A recorder J is connected to the thermocouple C and to the driver F. A programmer K may be connected, if desirable, to the furnace B within which the specimen A to be tested may be positioned although in some applications the furnace B may be totally eliminated.

The improvement of this invention is directed primarily to the specimen clamps or grips 23 that are each releasably mounted on the freely-extending terminal ends 24 and 25 of the active and passive arms 11 and 14. The specimen or sample 26 to be tested in the dynamic mechanical analyzer 10 is supported by the clamps or grips 23 that are spaced laterally from each other in one position of orientation as shown in FIG. 1.

Each specimen clamp 23 has a body member 27 in which there is a base section 28 from which base section 28 a pair of laterally spaced-apart and projecting guide lugs 29 and 30 extend in parallel relationship. An arm-end seating tab 31 extends at the end of the base section in a direction opposite from guide lugs 29 and 30 to engage the end 32 or top surface 33 of the arm ends 24 and 25 as will be described more fully hereafter. The guide lug 30 is provided with a threaded opening 34 for cooperatively receiving and retaining the headed and threaded clamping screw 35 therein. A series of spaced threaded openings 36 is provided adjacent to one side 37 of the guide lug 30 for cooperatively receiving the positioning or locating stop 38 which will center the specimen 26 to be tested depending upon its width.

Threaded holes 39 and 40 are provided in the guide lug 30 for cooperatively receiving the screws 41 and 42, respectively, which will serve as guide means for the sample positioning member 43 that will be guidably and slidably retained between the guide lugs 29 and 30 of the body member. The vertical web 44 of the sample positioning member 43 is provided with a stabilizing or blind opening 45 that will cooperatively receive and seat the reduced end 46 of the threaded member 35 therein. The series of vertical openings 47 in the web coincide with the opening 36 in the guide lug 30 for cooperatively receiving the stop member 38 through the shank 48 thereof. The guide flange 49 on the web 44 is provided with an enlongated open slot 50 for cooperatively receiving the threaded guide member 41 therein. The opposite end of the member 43 is provided with an elongated flange 51 in which the open elongated slot 52 will receive the threaded fastening 42 therein. The opposite end of the flange 51 from the slot 52 is also provided with an open elongated slot 53 for cooperatively receiving the threaded guide member 54 that is threadably retained in the opening 55 formed in the bottom of the guide lug 29, as shown in FIG. 5.

As shown in FIG. 6, a series of spaced threaded openings 56, 57 and 58 is provided in the base section 28 adjacent to the tab 31 with the threaded opening 59 being spaced at the opposite end in horizontal alignment with the opening 57. The distance from openings 56 to 58 is equal to that distance from opening 57 to opening 59. In the position shown in FIG. 1, the body member 27 may be securely fastened to the arm ends 24 and 25 through the threaded openings 56 and 58 by the fastening members 60 to support the specimen 26 to be tested in the vertical position as shown in FIGS. 1, 2 and 4. The specimen clamps 23 may support the specimen 26 in a horizontal or flat position by rotating the specimen grips 23 through 90 degrees and mounting them so that the positioning tabs 31 of the grips 23 contact the upper end surfaces 33 on each freely-extending arm 11 and 14 while the threaded openings 57 and 59 in the base section 28 of the body member 27 are engaged by the fastening means 60 that are passed through openings 57 and 59 in the base section 28 to secure the individual body members in position on the arm ends 24 and 25.

As shown in FIGS. 2-4, the specimen 26 to be tested is clamped by the grips 23 and retained in the clamped position by means of the sample positioning member 43 which is forced against the specimen 26 by means of the threaded fastening member 35 which, with the guide lug 29 forms a vise to retain the specimen 26 firmly in position. The spacing shank 48 located in the lower opening 36 will serve to act as a stop to limit the positioning downwardly of the specimen 26 between the clamps or grips 23. In those test specimens that are shorter in the vertical distance, the positioning stop 38 may be raised to a higher opening 36 in order to centralize the positioning of the test specimen 26.

The sample positioning member 43 is guidably retained in the body member for displacement between the guide lugs 29 and 30 by means of the cooperation of the guide fastening members 41, 42 and 54 within the elongated slots 50, 52 and 53, respectively, in the flanges 49 and 51. The fastening members 41, 42 and 54 may be tightly secured, if necessary, depending upon the sample being tested, and to prevent any possible skewing of the specimen to be tested.

With the length of the specimen being predetermined by the spacing between the clamps or grips 23, the thickness of the specimen may be readily accommodated by the displacement of the members 35. The vertical distance may be readily accommodated by means of the adjustments in the openings 36 to suit the particular specimen.

It will be readily apparent that the spacing and the positioning of the openings as well as the guide lugs may vary depending upon the particular specimens to be tested and variations are contemplated.

I claim:

1. In a dynamic mechanical analyzer to support a specimen for testing, said analyzer having a pair of spaced sample arms displaceable relative to each other and having terminal freely extending spaced-apart ends, one of said sample arms being driven and the other counterbalanced, said driven arm having an electromechanical transducer, and means to determine the frequency and amplitude of oscillation of said driven arm, the improvement comprising; a pair of clamps for releasably supporting a specimen to be tested and said clamps and specimen being retained by said sample arms adjacent to the terminal spaced-apart ends thereof, each clamp having a body member, said body member having a base section, said base section having a pair of laterally spaced-apart projecting and cooperating guide lugs, said guide lugs having a specimen stop means for prepositioning a specimen to be tested, said specimen stop means being removable and positionable at selected spaced increments to accommodate a specimen to be centralized relative to said guide lugs and specimen positioning means for testing, means on said base section for mounting said body member to an arm terminal end, a specimen means cooperatively and slidably retained by said guide lugs, means on one of said guide lugs for displacing said specimen positioning means laterally between said guide lugs to releasably clamp a specimen to be tested.

2. In a dynamic mechanical analyzer as claimed in claim 1, one of said guide lugs on said base section having a series of spaced openings, said specimen positioning means having a series of spaced openings coinciding with said spaced openings in at least one of said base section guide lugs, and a removable member for insertion into a selected pair of aligned openings, one opening in said base section guide lug and one opening in said specimen positioning means for limiting the position of a specific specimen size to be tested and for centralizing the specimen in the clamps.

3. In a dynamic mechanical analyzer to support a specimen for testing, said analyzer having a pair of spaced sample arms displaceable relative to each other and having terminal freely extending spaced-apart ends, one of said sample arms being driven and the other counterbalanced, said driven arm having an electrochemical transducer, and means to determine the frequency and amplitude of oscillation of said driven arm, the improvement comprising; a pair of clamps for releaseably supporting a specimen to be tested and said clamps and specimen being retained by said sample arms adjacent to the terminal spaced-apart ends thereof, each clamp having a body member, said body member having a base section, said base section having a pair of laterally spaced-apart projecting and cooperating guide lugs, means on said base section for mounting said body member to an arm terminal end, a specimen positioning means cooperatively and slidably retained by said guide lugs, means on one of said guide lugs for displacing said specimen positioning means laterally between said guide lugs to releasably clamp a specimen to be tested, said specimen positioning means having terminal transverse portions engaging at least one of said guide lugs, said transverse portions each having a guide slot, and a guide stud cooperatively received in each of said guide slots mounted on said guide lugs to limit skewing of said specimen positioning means.

4. In a dynamic mechanical analyzer as claimed in claim 3, and at least one of said terminal transverse portions extending to engage a pair of guide lugs and having a guide slot in said terminal portion for each cooperating with each guide lug, and a guide stud in each guide lug cooperatively received in each guide slot on said one terminal transverse portion.

* * * * *